(12) United States Patent
Hu et al.

(10) Patent No.: US 10,327,652 B2
(45) Date of Patent: Jun. 25, 2019

(54) OPTO-PHYSIOLOGICAL SENSOR AND METHOD OF ASSEMBLY

(71) Applicant: LOUGHBOROUGH UNIVERSITY, Leicestershire (GB)

(72) Inventors: Sijung Hu, Leicestershire (GB); Vicente Azorin-Peris, Leicestershire (GB)

(73) Assignee: Loughborough University, Leicestershire (GB)

( * ) Notice: Subject to any disclaimer, the term of this patent is extended or adjusted under 35 U.S.C. 154(b) by 0 days.

(21) Appl. No.: 15/029,984

(22) PCT Filed: Oct. 15, 2014

(86) PCT No.: PCT/GB2014/053095
§ 371 (c)(1),
(2) Date: Apr. 15, 2016

(87) PCT Pub. No.: WO2015/056007
PCT Pub. Date: Apr. 23, 2015

(65) Prior Publication Data
US 2016/0278646 A1    Sep. 29, 2016

(30) Foreign Application Priority Data

Oct. 17, 2013  (GB) .................................. 1318390.0

(51) Int. Cl.
*A61B 5/00* (2006.01)
*A61B 5/024* (2006.01)
(Continued)

(52) U.S. Cl.
CPC ........ *A61B 5/02427* (2013.01); *A61B 5/0015* (2013.01); *A61B 5/01* (2013.01);
(Continued)

(58) Field of Classification Search
CPC ..... A61B 5/02427; A61B 5/0015; A61B 5/01; A61B 5/11; A61B 5/14552; A61B 5/7225;
(Continued)

(56) References Cited

U.S. PATENT DOCUMENTS 4,905,702 A    3/1990 Foss
5,188,108 A *  2/1993 Secker ............... A61B 5/04485
                                                  356/41
(Continued)

FOREIGN PATENT DOCUMENTS

CN    1638690 A    7/2005
EP    0442011 A1   8/1991
(Continued)

OTHER PUBLICATIONS

Allen; Photoplethysmography and its application in clinical physiological measurement; Physiol. Meas.; 28(3); pp. R1-R39; Mar. 2007.
(Continued)

*Primary Examiner* — Paula J Stice
(74) *Attorney, Agent, or Firm* — Shay Glenn LLP (57) ABSTRACT

A method of assembling an opto-physiological (OP) sensor comprises: (i) modelling the opto-physiological properties of at least one body tissue type to be monitored; (ii) determining, through application of the model, an optimal optical design for an opto-physiological (OP) sensor operable to monitor the opto-physiological properties of the at least one body tissue type; and (iii) making the OP sensor to the determined optical design. The optimal optical design for the OP sensor comprises: (i) determining the optimum separation of each of a plurality of light sources from a photodetector, based on modelled optical path lengths for light travelling from each light source, through the body
(Continued)

tissue type to be monitored, to the photodetector; and (ii) locating light sources of different wavelengths at different distances from the photodetector.

4 Claims, 5 Drawing Sheets

(51) Int. Cl.
| | |
|---|---|
| *A61B 5/01* | (2006.01) |
| *A61B 5/1455* | (2006.01) |
| *A61B 5/11* | (2006.01) |
| *A61B 5/021* | (2006.01) |
| *A61B 5/08* | (2006.01) |
| *G16H 50/50* | (2018.01) |

(52) U.S. Cl.
CPC ............ *A61B 5/11* (2013.01); *A61B 5/14552* (2013.01); *A61B 5/7225* (2013.01); *A61B 5/742* (2013.01); *A61B 5/7475* (2013.01); *A61B 5/0002* (2013.01); *A61B 5/021* (2013.01); *A61B 5/02405* (2013.01); *A61B 5/0816* (2013.01); *A61B 5/7203* (2013.01); *A61B 5/7221* (2013.01); *A61B 2560/0223* (2013.01); *A61B 2562/0242* (2013.01); *A61B 2562/12* (2013.01); *G16H 50/50* (2018.01)

(58) Field of Classification Search
CPC ... A61B 5/742; A61B 5/02154; A61B 5/0261; A61B 5/1079; A61B 5/1455
See application file for complete search history.

(56) References Cited

U.S. PATENT DOCUMENTS

| | | |
|---|---|---|
| 6,550,933 B1 | 4/2003 | Panz |
| 2002/0082489 A1 | 6/2002 | Casciani et al. |
| 2005/0020892 A1 | 1/2005 | Acosta et al. |
| 2009/0247083 A1 | 10/2009 | Pay |
| 2010/0081901 A1 | 4/2010 | Buice et al. |
| 2012/0095305 A1 | 4/2012 | Wang et al. |

FOREIGN PATENT DOCUMENTS

| | | |
|---|---|---|
| EP | 0992214 A2 | 4/2000 |
| EP | 2679981 A1 | 1/2014 |
| JP | 2004-073559 A | 3/2004 |
| WO | WO2007/097702 A1 | 8/2007 |
| WO | WO2009/030934 A2 | 3/2009 |
| WO | WO2010/038122 A1 | 4/2010 |
| WO | WO2011/026669 A1 | 3/2011 |

OTHER PUBLICATIONS

Alzahrani et al.; An Effective Solution to Reduce Motion Artefact in New Generation Reflectance Pulse Oximeter; Electronics Communications and Photonics Conf. (SIECPC); pp. 1-5; Apr. 27-30, 2013.

Azorin-Peris et al.; A Monte Carlo Platform for the Optical Modelling of Pulse Oximetry; Applied Physics Letters, SPIE, vol. 6446; 6 pgs.; Biomedical Applications of Light Scattering, Adam Wax, Vadim Backman, Editors, 64460T; Feb. 2007.

Hu et al.; A study of opto-physiological modelling to quantify tissue absorbance in imaging photoplethysmography; 32nd Annual International Conf. of the IEEE EMBS; Buenos Aires, Argentina; pp. 5776-5779; Aug. 31-Sep. 4, 2010.

Hu et al.; Development of effective photoplethysmographic measurement techniques: from contact to non-contact and from point to imaging; 31st Annual International Conf. of the IEEE EMBS; Minneapolis, MN, USA; pp. 6550-6553; Sep. 2-6, 2009.

Kumar et al.; Optimal probe geometry for near-infrared spectroscopy of biological tissue; Applied Optics; 36(10); pp. 2286-2293; Apr. 1997.

Shi et al.; A Preliminary Attempt to Understand Compatibility of Photoplethysmographic Pulse Rate Variability with Electrocardiogramic Heart Rate Variability; J Med. Biolog. Eng.; 28(4); pp. 173-180; Sep. 2008.

Shi et al.; Analysis of pulse rate variability derived from photoplethysmography with the combination of lagged Poincare plots and spectral characteristics; Med. Phys.; 31(7); pp. 866-871; Sep. 2009.

Shi et al.; Insight into the dicrotic notch in photoplethysmographic pulses from the finger tip of young adults; J Med. Eng. Tech.; 33(8); pp. 628-633; Aug. 2009.

Shi et al.; Non-contact Reflection Photoplethysmography towards Effective Human Physiological Monitoring; J Med. Biol. Eng.; 30(3); pp. 161-167; 2010 (accepted: Nov. 12, 2009).

Zhang et al.; Electrically conductive adhesive enable to manufacture high performance patch probe for non-invasive physiological assessment; Proc Electronics System-Integration Tech Conf (ESTC); Amsterdam, Netherlands; pp. 1-4; Sep. 17-20, 2012.

\* cited by examiner

OPTO-PHYSIOLOGICAL SENSOR AND METHOD OF ASSEMBLY

FIELD OF THE INVENTION

The present invention relates to an opto-physiological (OP) sensor and a method of assembling such a sensor. Aspects of the invention also relate to a physiological sensor system comprising the OP sensor and, in particular, to the geometrical distribution of associated illumination sources.

BACKGROUND TO THE INVENTION

Photoplethysmography (PPG) is a non-invasive optical technique for monitoring variation in blood volume or blood flow near the surface of the skin to determine various physiological parameters. The principle uses an illumination source and a photodetector to measure changes in intensity as light is passed through or reflected from body tissue. The detected optical signals are then analysed and correlated with the pulsation of blood through the body, as stimulated by the heartbeat. More background information about PPG can be found in the topical review "Photoplethysmography and its application in clinical physiological measurement", John Allen, Physiol. Meas. 28 (2007) R1-R39, as well as in the following papers co-written by the present inventors and their colleagues:

"Non-contact Reflection Photoplethysmography towards Effective Human Physiological Monitoring", Shi, P., Azorin Peris, V., Echiadis, A., Zheng, J., Zhu, Y., Cheang, P. Y. S., Hu, S.*, J Med. Biol. Eng. Vol.30 Iss 30 (2010): 161-167;

"Insight into the dicrotic notch in photoplethysmographic pulses from the finger tip of young adults", Shi, P., Hu, S.*, Zhu, Y., Zheng, J., Qiu, Y., Cheang, P. Y. S., J Med Eng Tech, Vol. 31, Iss 8 (2009), 628-633;

"Analysis of pulse rate variability derived from photoplethysmography with the combination of lagged Poincaré plots and spectral characteristics", Shi, P., Zhu Y., Allen, J., Hu, S.*, Med Eng. Phys. 31 (2009) 866-871, doi: 10.1016/j.medengphy.2009.05.001;

"A Preliminary Attempt to Understand Compatibility of Photoplethysmographic Pulse Rate Variability with Electrocardiogramic Heart Rate Variability", Shi, P., Hu, S., Zhu, Y., J Med. Biolog. Eng., Vol.28, Iss 4 (2008): 173-180;

"A Monte Carlo Platform for the Optical Modelling of Pulse Oximetry", Azorin-Peris, V., Hu, S.*, Smith, P. R, Applied Physics Letters, SPIE, Vol.6446 (2007), pp.64460T;

"An Effective Solution to Reduce Motion Artefact in New Generation Reflectance Pulse Oximeter", Alzahrani, A., Hu, S., SIECPC-Apr 2013;

"Electrically conductive adhesive enable to manufacture high performance patch probe for non-invasive physiological assessment", Zhang, X., Hu, S.*, Liu, C., Azorin-Peris, V., Imms, R Proc Electronics System-Integration Tech Conf (ESTC) 2012;

"A study of opto-physiological modelling to quantify tissue absorbance in imaging photoplethysmography", Hu, S.*, Azorin Penis V., Zheng J., Proc. IEEE EMBC 32, 2010, 1: 5776-5779; and "Development of effective photoplethysmographic measurement techniques: from contact to non-contact and from point to imaging", Hu, S.*, Azorin Penis V., Echiadis A., Zheng J., and Shi P., Proc. IEEE EMBC 31, 2009, 1: 6550-6553.

In an earlier application, WO2009/030934 (incorporated herein by reference), the applicants describe a method of forming an image comprising sequentially illuminating a target with a plurality of illumination pulses and consolidating the image pulse signals to provide a real time image of blood pulsing, which is dependent upon blood oxygen saturation within a blood circulation system.

Opto-physiological technology (including PPG) is applicable to the global mobile health market, which is growing rapidly in developed countries in response to the rising incidence of lifestyle induced chronic diseases and ageing populations. The two main applications of this technology are: i) self-monitoring, for example, for sports performance or to maintain or improve general wellbeing and fitness levels; and ii) clinician-monitoring to capture important health parameters of chronically ill patients or those undergoing post-operative care. In addition, monitoring may be performed to identify or confirm underlying illnesses or to monitor the vital parameters of at-risk patients to track underlying conditions and provide an early warning signal in order to prevent exacerbation.

In relation to current PPG systems, pulse oximetry devices (which determine blood oxygen saturation) are most common. However, these are often inaccurate as they do not take into account the light scattering effects of live tissue, motion induced artefacts or the effects of sweat, skin creams or sprays.

In the consumer fitness market, electrical chest-strap based continuous heart rate monitoring systems are often employed. However, these tend to be uncomfortable and obtrusive making them unpopular for frequent use. Other wearable monitoring systems are emerging in the market, including wristwatch-based sensors that can measure individual parameters such as heart rate and/or respiratory rate. However, no wearable sensor is currently available that can simultaneously measure a wider range of physiological parameters, including blood oxygen saturation.

It is therefore an aim of the present invention to provide an opto-physiological (OP) sensor and a method of assembling the same, which helps to address the afore-mentioned problems.

SUMMARY OF THE INVENTION

In accordance with a first aspect of the present invention there is provided a method of assembling an opto-physiological (OP) sensor comprising:
  modelling the opto-physiological properties of at least one body tissue type to be monitored;
  determining, through application of the model, an optimal optical design for an opto-physiological (OP) sensor operable to monitor the opto-physiological properties of the at least one body tissue type; and
  making the OP sensor to the determined optical design;
  wherein the optimal optical design for the OP sensor comprises:
    determining the optimum separation of each of a plurality of light sources from a photodetector, based on modelled optical path lengths for light travelling from each light source, through the body tissue type to be monitored, to the photodetector; and
    locating light sources of different wavelengths at different distances from the photodetector.

Embodiments of this aspect of the invention therefore provide a method of assembling a non-invasive OP sensor (including the design thereof) which is ideally configured for use with a body tissue type to be monitored so as to allow optical data, relating to the physiological parameters being studied, to be reliably and accurately obtained. The OP sensor may be designed for applications requiring opto-physiological assessment (e.g. to monitor heart rate, respiration rate, blood oxygen saturation, heart rate variability, pulse wave velocity, blood pressure or body temperature), biofeedback or spectrophotometrics. In a particular embodiment, the OP sensor may be designed for the consumer fitness market (e.g. to provide continuous heart rate monitoring via a lightweight sensor worn on the body). In other applications, the OP sensor may be designed for use in the clinical monitoring of patients. In certain embodiments, the detected parameter may be used to monitor or track disease progression (e.g. of cardiovascular disease or diabetes).

It will be understood that the model will essentially provide knowledge of how an optical signal will interact with the body tissue being monitored.

The method also determines the optimum separation of each of the light sources from the photodetector, based on the calculated optical path lengths through the body tissue type.

Notably, the optimal optical design for the OP sensor comprises locating light sources of different wavelengths at different distances from the photodetector.

The optimal optical design for the OP sensor may comprise use of multiple light sources configured to generate light at the same wavelength or waveband and wherein the sensor is configured to select one or more of said multiple light sources for use in an opto-physiological measurement based on captured radiation quality at the photodetector.

Furthermore, the optimal optical design for the OP sensor may comprise the use of a plurality of light sources configured to generate light at two or more wavelengths or wavebands and each light source may be positioned at a distance from a photodetector that is a function of the wavelength of said light source. More specifically, the position of each light source will determined on the basis of the expected optical path length of light passing through the body tissue type from each light source to the photodetector.

The at least one body tissue type may comprise one or more of: a tissue site (for example, but not limited to, a finger, neck, toe, ear, temple, wrist, palm, arm, hip, thigh, abdomen, forehead, face, scalp, back or chest), a tissue colour, a tissue thickness, a tissue age and a tissue condition (e.g. dry, wet, sweaty, burnt, coated with a skin cream or spray). The opto-physiological properties of the at least one body tissue type may comprise one or more of: a coefficient of absorption, a coefficient of scattering, a refractive index and optical density.

In some embodiments of the invention, the sensor may be designed for a particular use (e.g. on a particular tissue site). In other embodiments, the sensor may be designed for multiple possible uses (e.g. on multiple possible tissue sites). Alternatively, an array of sensors may be provided for use on one or more tissue sites.

The model may be based on radiative transport theory. The model may comprise a geometric model of the body tissue type along with optical properties of the body tissue type. The optical properties may be considered at one or more wavelengths.

The mathematical model may comprise the use of a finite element method to derive effective opto-physiological parameters from a virtual representation of the at least one body tissue type.

The step of determining the optimal optical design for the OP sensor may comprise using the model to determine one or more wavelengths or wavebands of light for optimal transmission through or reflection from the body tissue type.

The step of determining the optimal optical design for the OP sensor may comprise using the model to determine an arrangement and/or intensity of light sources for optimal illumination of the body tissue type.

Optical path lengths will be calculated at a plurality of wavelengths.

The model may comprise defining infinitesimal optical power dP that is transmitted through to point (x, y) on a surface of the body tissue type as per Equation 10:

$$\rho(\lambda,l'(x',y')):dP(\lambda,x,y)=\iint I_0(\lambda,x',y') \times e^{-\rho(\lambda,l'(x',y'))} dx'dy' \quad [\text{Eq. 10}]$$

wherein $I_0(\lambda, x, y)$ represents the total light that enters across the entire surface of the body tissue type and is subject to exponential decay, which is a function of the optical density $\rho(\lambda)$ of the body tissue type;

wherein a source-detector separation is defined in terms of a light source at point $(x_s, y_s)$ and an arbitrary detector at point (x, y) on the surface of the body tissue type, such that $l'(x,y)=\sqrt{(x-x_s)^2+(y-y_s)^2}$; and wherein for a detector of a finite rectangular area on the surface of the body tissue type defined by vectors x and y, spanning from $x_-$ to $x_+$ and from $y_-$ to $y_+$, the optical power received by the detector is as per Equation 11:

$$P(\lambda,x,y)=\int_{x_-}^{x_+}\int_{y_-}^{y_+} dP(\lambda,x_d,y_d) dx_d dy_d \quad [\text{Eq. 11}]$$

The model may comprise defining an optical response of a dynamic and multi-layered body tissue type in terms of its dynamic optical density $\rho(\lambda, l', t)$, using a normalised physiological pulse function $\psi(t)$, and absorption, scattering and pulsatility coefficients $\mu_{ai}(\lambda)$, $\mu_{si}(\lambda)$ and $\mu_{pi}(\lambda)$ respectively, where the layer number i ranges from 1 to N as per Equation 13:

$$\rho(\lambda,l',t)=\Sigma_{i=1}^{N}(\mu_{ai}(\lambda) \times L(\mu_{si}(\lambda),l') \times (1+\mu_{pi}(\lambda) \times \psi(t))) \quad [\text{Eq. 13}]$$

The model may comprise separation of static $\overline{\rho}(\lambda, l')$ and dynamic $\tilde{\rho}/(\lambda,l',t)$ components of Equation 13 as per Equations 14 to 16:

$$\rho(\lambda,l',t)=\overline{\rho}(\lambda,l')+\tilde{\rho}(\lambda,l',t) \quad [\text{Eq. 14}]$$

$$\overline{\rho}(\lambda,l)=\Sigma_{i=1}^{N}(\mu_{ai}(\lambda) \times L(\mu_{si}(\lambda),l')) \quad [\text{Eq. 15}]$$

$$\tilde{\rho}(\lambda,l',t)=\Sigma_{i=1}^{N}(\mu_{ai}(\lambda) \times L(\mu_{si}(\lambda),l') \times \mu_{pi}(\lambda) \times \psi(t)) \quad [\text{Eq. 16}]$$

The model may comprise using a sum rule of integration on Equations 10 and 11 to define static $\overline{P}(\lambda,x,y)$ and dynamic $\tilde{P}(\lambda,x,y,t)$ components of transmitted optical power for a rectangular detector defined by vectors x and y as per Equations 17, 19 and 21:

$$P(\lambda, x, y, t) = \overline{P}(\lambda, x, y) + \tilde{P}(\lambda, x, y, t) \quad [\text{Eq. 17}]$$

$$\overline{P}(\lambda, x, y) = \int_{x_-}^{x_+}\int_{y_-}^{y_+}\left(\iint I_0(\lambda, x', y') \times e^{-\overline{\rho}(\lambda,l'(x',y'))} dx' dy'\right) dx_d dy_d \quad [\text{Eq. 19}]$$

$$\tilde{P}(\lambda, x, y, t) = \int_{x_-}^{x_+}\int_{y_-}^{y_+}\left(\iint I_0(\lambda, x', y') \times e^{-\tilde{\rho}(\lambda,l'(x',y'),t)} dx' dy'\right) dx_d dy_d \quad [\text{Eq. 21}]$$

The model may comprise defining a quality Q of a detected signal in terms of its normalised peak dynamic power as per Equation 22:

$$Q(\lambda) \propto |\min_t(\tilde{P}(\lambda,x,y,t))|/\overline{P}(\lambda,x,y) \quad [\text{Eq. 22}]$$

wherein a peak dynamic power is defined using a minimum value of the dynamic power as the strongest power transient originates at systolic heart pressure, which manifests as a trough in the optical signal acquired from the sensor.

The model may comprise defining an optimum source-detector separation l'(λ) for a light source at wavelength λ as per Equation 23:

$$l'(\lambda) = \max_{(x,y)}(|\min_t(\tilde{P}(\lambda, x-x, y-y, t)|/\bar{P}(\lambda, x-x, y-y))$$ [Eq. 23]

The model may comprise assuming cylindrical symmetry and optical homogeneity of the body tissue type such that an optimum source-detector separation l' (λ) is expressed as a circle centred on the position of the light source $(x_s, y_s)$, or conversely centred on the position of the detector $(x_d, y_d)$, as per Equation 24:

$$l'(\lambda) = \sqrt{(x-x_s)^2 + (y-y_s)^2} = \sqrt{(x-x_d)^2 + (y-y_d)^2}$$ [Eq. 24]

The light sources may or may not generate visible light. For example, the light sources may have wavelengths in the range of approximately 450 nm to 1100 nm (corresponding to visible to near-infrared radiation).

The OP sensor may be configured for contact with the body tissue to be monitored. In which case, the sensor may be provided in the form of a wearable patch or wristwatch. Alternatively, the OP sensor may be configured for non-contact with the body tissue to be monitored. In which case, the sensor may be provided on a dedicated device (e.g. for clinical use) or may be incorporated into a mobile phone, camera, tablet, PDA, pair of glasses or other handheld device.

In accordance with a second aspect of the present invention there is provided an opto-physiological (OP) sensor assembled by the method according to the first aspect of the invention.

In accordance with a third aspect of the present invention there is provided an opto-physiological (OP) sensor comprising:
  a plurality of light sources; and
  at least one photodetector configured to capture radiation originating from one or more of said light sources, after light from said light source has travelled through a body tissue type to be monitored,
  wherein the plurality of light sources are located relative to the photodetector at positions determined by a model of the opto-physiological properties of the body tissue type to be monitored,
  wherein the optimum separation of each light source from the photodetector is based on modelled optical path lengths for light travelling from each light source, through the body tissue type to be monitored, to the photodetector; and
  wherein light sources of different wavelengths are located at different distances from the photodetector.

Multiple light sources may be configured to generate light at the same wavelength or waveband and the sensor may be operable to select one or more of said multiple light sources for use in an opto-physiological measurement based on the captured radiation quality.

The plurality of light sources may be configured to generate light at two or more wavelengths or wavebands and each light source may be positioned at a distance from the photodetector that is a function of the wavelength of said light source.

The plurality of light sources may be modulated. For example, the plurality of light sources may be configured for amplitude modulation so as to provide a multiplexed signal to the body tissue and which, once detected, can be de-multiplexed to enable the measurement of signals from each individual light source or set of light sources (i.e. channels). The amplitude modulation may be performed, for example, using a square wave (i.e. DC) characteristic or a sine wave modulation and may comprise use of a lock-in amplifier. As an example, a first channel may be activated for a finite period of time then deactivated and these steps repeated for each other channel. The entire process may be repeated a number of times to yield multiple samples from each channel. In particular embodiments, the capture of each signal sample from the photodetector may begin a predetermined time after the respective channel has been activated and may end a predetermined time before the respective channel has been deactivated to ensure an optimum stability and signal-to-noise ratio in the resultant signals.

Accordingly, in some embodiments, a multi-time gating approach (MTG) may be applied (e.g. to in-vivo measurements) to modulate the operation of the plurality of light sources (either individually or in groups with common wavelengths) and to demodulate the captured signals from the photodetector.

The OP sensor can be thought of as an optical biosensor configured to monitor the in-vivo opto-physiological properties of body tissue.

In a particular embodiment, a photodetector is positioned centrally within an array of light sources and each light source is positioned at a distance from the photodetector that is a function of the wavelength of said light source. For example, each light source may be positioned on the circumference of a circle that is centred on the photodetector, wherein the radius of each circle is a function of the wavelength of the respective light source.

In particular embodiments, a camera may constitute the photodetector positioned centrally within an array of light sources and may be used for contact or for non-contact imaging. In some embodiments, the camera may include a controllable flash light, and the flash light may be used as a light source.

The OP sensor of the second or third aspects of the invention may further comprise a controller operable to activate and deactivate the plurality of light sources based on a measured signal from the photodetector. In particular embodiments, the controller is operable to modulate the plurality of light sources by selectively activating and deactivating them to create a time-division multiplexed illumination. The controller may subsequently demodulate the response from the photodetector to determine the signals deriving from each light source or group of light sources operated simultaneously (e.g. at the same wavelength). The controller may then analyse the derived signals to determine those most suitable for use in obtaining the desired opto-physiological properties.

The plurality of light sources may be configured to generate light at two or more wavelengths or wavebands (e.g. an individual light source may be configured to generate light at a particular wavelength, different to another light source, or an individual light source may be adaptable to produce light at different wavelengths). This is advantageous in that different wavelengths will interact differently with the body tissue being monitored (e.g. certain wavelengths may provide stronger signals when used with darker skin colours) and therefore it is useful to be able to select the wavelengths producing the strongest or most reliable signals for subsequent analysis in order to determine the opto-physiological properties of interest.

Additionally or alternatively, multiple (redundant or reference) light sources may be configured to generate light in the same wavelength or waveband. This may provide increased robustness should one light source be damaged or misaligned, resulting in a poor quality signal being detected by the photodetector.

In certain embodiments, the use of multiple wavelengths may be required to achieve a desired signal quality and/or to determine certain physiological parameters for which it is necessary to acquire multiple signals at multiple wavelengths. In some tissue locations, some particular wavelengths may not be suitable to acquire the desired signal (i.e. they may not penetrate deep enough into the tissue or may be scattered by the tissue surface), and therefore the use of multiple wavelengths can ensure a more reliable acquisition of signals and a more robust overall performance of the sensor.

In general, the use of multiple light sources and/or multiple wavelengths can greatly increase the functionality and adaptability of the sensor such that a single sensor can be used to accurately measure the opto-physiological properties of multiple tissue types. More specifically, the use of multiple light sources and/or multiple wavelengths may allow a more reliable measurement of vital signs from multiple locations on the subject's tissue.

With a known distribution of light sources on the tissue (e.g. spaced around concentric circles with a 90 degree separation between each light source on the same circle), the OP model may be used to determine motion characteristics. For example, for a single wavelength, a degree of tilt between the sensor and tissue can be estimated by looking at the relative changes in intensity from each light source with respect to the overall intensity of all light sources. The mean path length of light travelling from the light sources via the tissue to the photodetector may be employed to calculate an accurate quantification of the motion artefact. Furthermore, a motion sensor (e.g. 3D accelerometer) may be provided on the sensor to provide an alternative description of any motion, which may be used as a reference for comparison with the optically derived characteristics of the motion.

The plurality of light sources may be configured to generate incoherent or semi-coherent electromagnetic radiation.

The at least one photodetector may be configured to capture radiation originating from one, some or all of the light sources, after the radiation has travelled through (by reflection or transmission) the body tissue being monitored.

The OP sensor may be configured (e.g. through multiplexing) such that independent signals are obtainable from the exclusive contribution of each individual light source to an output from the at least one photodetector. Alternatively, independent signals may be obtainable from the contribution of each individual wavelength or waveband of light to an output from the at least one photodetector.

The controller may be configured to selectively activate and/or deactivate light sources based on a signal quality metric. The signal quality metric may analyse each independent signal and adjust or disable the light sources from which the independent signal is derived so as to save energy and/or provide optimum reliability of the output from the at least one photodetector. In this regard, the controller may be configured to implement the method according to the fourth aspect of the invention (defined below).

It will be understood that the use of multiple light sources can ensure that there is more than one available pathway for light to travel through the body tissue to be monitored to the photodetector. It is therefore possible for the signal quality metric to be applied so as to separate or eliminate noisy or poor quality signals so that the output from the photodetector is more accurate and reliable. Furthermore, the use of multiple signal pathways means there is a potential for signal averaging or other processing (e.g. if two or more robust signals are detected). Such techniques can also be applied to improve the sensor's resistance to motion induced artefacts.

Embodiments of the OP sensor may therefore be configured to automatically adjust the sensor characteristics for the body tissue being monitored (e.g. by changing the light sources or wavelengths activated and the intensity of the same) during use so as to optimise the quality of the signals detected. Thus, not only is the sensor designed through application of an opto-physiological model of the tissue type (or types) to be monitored but the sensor is also able to dynamically adjust its settings during use, for example, to take into account the age of the user or an accumulation of sweat or creams applied to the skin.

The OP sensor may be powered via an integrated power source such as a battery. Alternatively, the OP sensor may be powered via a wireless power transmission such as an inductive power coupling.

The OP sensor may be configured for wireless communication with a base station or host server.

The OP sensor may be configured as an adhesive patch which can be directly attached to the body tissue to be monitored. The patch may be of any appropriate size but conveniently may be coin-sized. Advantageously, the patch will be lightweight, unobtrusive and waterproof so as not to hinder or inconvenience a person wearing it.

The OP sensor may be configured as a low-cost disposable sensor or for long-term or repeat use.

The OP sensor may be configured for continuous (dynamic) data collection (e.g. for several hours or days) without the need for re-charging.

In accordance with a fourth aspect of the present invention there is provided a method of controlling an opto-physiological (OP) sensor comprising a plurality of light sources and at least one photodetector configured to capture radiation originating from one or more of said light sources, after light from said light source has travelled through body tissue to be monitored, the method comprising:

obtaining independent signals from the contribution of each individual light source to an output from the at least one photodetector;

performing one or more measurements of signal quality on each independent signal;

modifying the illumination intensities of each individual light source and repeating the measurements of signal quality;

further modifying the intensities of individual light sources whose independent signals have undergone a rise in signal quality and repeating the measurements of signal quality;

reversing the modification of intensities of individual light sources whose independent signals have undergone a drop in signal quality and repeating the measurements of signal quality;

fixing the intensities of individual light sources whose corresponding signals have reached a peak in signal quality; and selectively deactivating light sources whose independent signals are below a threshold value.

The method above may be applied to an OP sensor as defined in accordance with the second or third aspects of the invention.

It will be understood that the method of the fourth aspect of the invention effectively provides a method of optimising the intensity of each light source or wavelength used for the tissue type being monitored. The method may be applied as an initial configuration process when the sensor is first activated. Additionally or alternatively, the method may be applied periodically or when certain signal criteria is met so as to re-set the intensity of each light source during use.

In accordance with a fifth aspect of the present invention there is provided an opto-physiological (OP) system comprising:
an opto-physiological (OP) sensor according to the second or third aspect of the invention; and
an analyser configured to analyse a signal measured by the photodetector to determine at least one physiological parameter therefrom.

The analyser may employ an opto-physiological model to derive the physiological parameter from the measured signal. The opto-physiological model may be based on a fundamental understanding of the body tissue type being monitored (e.g. including a tissue site, colour, thickness, age or condition) so as to provide a more reliable interpretation of the optical signals and their correlation with blood volume as a function of time and/or blood composition.

The at least one physiological parameter may comprise: blood oxygen saturation, heart rate, pulse rate velocity, respiration rate, blood pressure, body temperature or an indication of a user's state or mood (e.g. active, sleeping, stressed).

The OP system may further comprise a user interface. The user interface may be configured to allow a user to select a physiological parameter to be monitored.

The OP system may further comprise a display arranged to communicate the determined physiological parameter to a user.

The OP system may further comprise a data management system for storing the determined physiological parameters.

The OP system may be configured as a standalone system, for example, embodied in a wristwatch, mobile telephone or other personal device. Additionally or alternatively, the OP system may be configured as a distributed system. For example, the sensor may constitute a client module (e.g. a patch or wristwatch) and one or more of the analyser, user interface, display and data management system may be provided via a remote base station or host server. In which case, the client module may be configured for wireless communication with the base station or host server. In addition, the OP system may be controllable via computer software (which may be provided in the form of a mobile phone or internet "app") so that a user can control the monitoring, recording, processing and display of the gathered data.

BRIEF DESCRIPTION OF THE DRAWINGS

Specific embodiments of the present invention will now be described with reference to the accompanying drawings, in which.

DETAILED DESCRIPTION OF CERTAIN EMBODIMENTS

Figure 1:
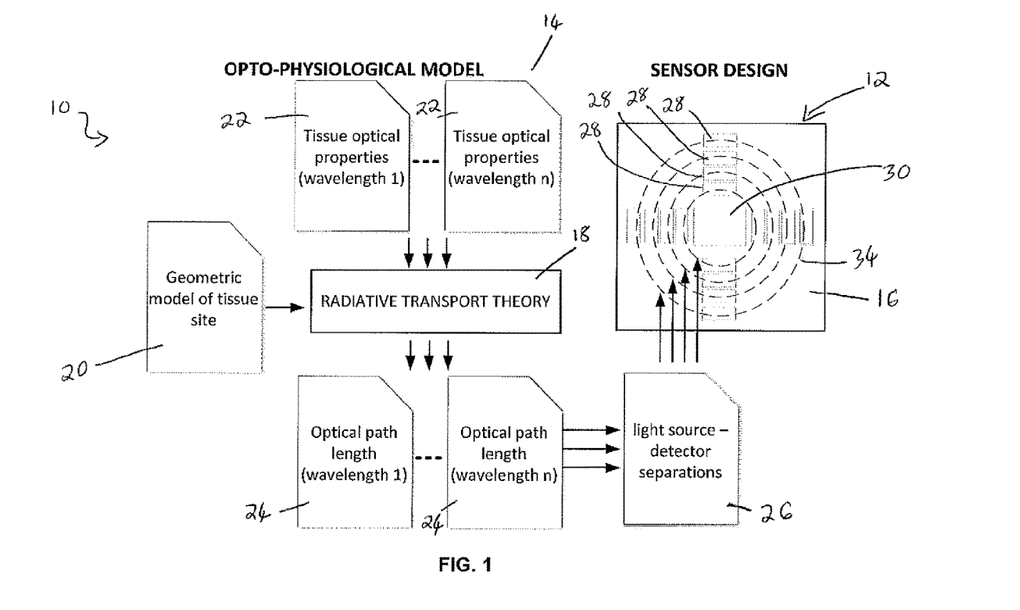
FIG. 1 shows a flow diagram of a method of designing an opto-physiological (OP) sensor in accordance with an embodiment of the present invention.

With reference to FIG. 1, there is illustrated a flow diagram 10 of a method of assembling (including designing) an opto-physiological (OP) sensor 12 in accordance with an embodiment of the present invention. The method comprises using an opto-physiological model 14 to mathematically model the opto-physiological properties of a body tissue type to be monitored and determining, through application of the model 14, an optimal optical design 16 for the opto-physiological (OP) sensor 12 so that it is operable to monitor the opto-physiological properties of the body tissue type. Thus, an aspect of the invention relates to a data-driven design approach for an optical sensing sub-system. Furthermore, the method includes making the OP sensor 12 to the determined optical design wherein the optimal optical design for the OP sensor 12 comprises: (i) determining the optimum separation of each of a plurality of light sources 28 from a photodetector 30, based on modelled optical path lengths for light travelling from each light source 28, through the body tissue type to be monitored, to the photodetector 30; and (ii) locating light sources 28 of different wavelengths at different distances from the photodetector 30.

In prior art systems, a Beer-Lambert model has been applied to relate the absorption of light to the properties of the material through which the light is travelling. However, it has been found that such an approach is too basic to be truly representative when trying to establish the opto-physiological properties of body tissue and therefore an opto-physiological model 14, which takes into account various properties of the body tissue to be monitored, is required.

As illustrated, the opto-physiological model 14 is based on radiative transport theory 18 and comprises a geometric model 20 of a body tissue site along with details of the optical properties 22 of the body tissue at various wavelengths (e.g. labelled 1 to n, where n is a positive integer). Based on this information, the model 14 calculates the optical path lengths 24 of light through the body tissue (at the various n wavelengths). The optical path lengths are then used to determine an optimum separation 26 of each light source 28 (at each of the n wavelengths) from the photodetector 30 so as to create an optimal design of OP sensor 12.

Equations for a suitable opto-physiological model 14 will now be described, where increasingly suitable examples of its constituents will be derived in order of complexity.

Light transmission through a medium (e.g. body tissue type) can be expressed as an exponential decay as per Equation 1.

$$I(\lambda) = I_0(\lambda) \times e^{-\rho(\lambda)\gamma} \qquad [\text{Eq. 1}]$$

This equation describes the exponential decay of the intensity of light at wavelength λ entering a medium $I_0(\lambda)$ as it travels through the medium with an optical density $\rho(\lambda)$. $I_0(\lambda)$ is kept constant throughout and can be expressed in terms of the light source intensity $I_S(\lambda)$ and the intensity of light reflected from the medium $I_R(\lambda)$ as per Equation 2.

$$I_0(\lambda)=I_S(\lambda)-I_R(\lambda) \quad [\text{Eq. 2}]$$

The loss of intensity due to reflection can alternatively be expressed using a coefficient of reflection ($C_R$) or transmission ($C_T$) as per Equation 3, where the coefficient has a value between 0 and 1.

$$I_0(\lambda)=(1-C_R)\times I_S(\lambda)=C_T\times I_S(\lambda) \quad [\text{Eq. 3}]$$

The optical density of the medium can be described in terms of its absorption coefficient $\mu_a(\lambda)$ and path length l as per Equation 4.

$$\rho(\lambda)=\mu_a(\lambda)\times l \quad [\text{Eq. 4}]$$

It will be understood that Equations 1 to 4 describe the case of a single optical path, where the transmitted intensity is entirely accounted for at the point of detection.

We now consider the more complex case of a highly scattering medium. When source light is scattered across a volume of tissue, an increased portion of the light is lost to absorption through an increase in mean optical path length to the detector, and a portion of this light may not fall within the surface of the photodetector. The optical density can be reformulated to account for such losses as per Equation 5.

$$\rho(\lambda)=\mu_a(\lambda)\times L(\mu_s(\lambda)) \quad [\text{Eq. 5}]$$

In this equation, L represents the effective path length of detected light and is a function of the scattering coefficient $\mu_s(\lambda)$ of the medium. The optical density can be further reformulated for the case of an N-layered medium with properties $\mu_{ai}(\lambda)$ and $\mu_{si}(\lambda)$ as per Equation 6, where the layer number i ranges from 1 to N.

$$\rho(\lambda)=\Sigma_{i=1}^{N}(\mu_{ai}(\lambda)\times L(\mu_{si}(\lambda))) \quad [\text{Eq. 6}]$$

We now consider the more rigorous case of an N-layered medium comprising a 2-dimensional (flat) outer surface on which the light source and photodetector can be located. The relationship between the intensities of light entering the medium $I_0$ and source light $I_S$ can be expressed as per Equation 7.

$$I_0(\lambda,x,y)=C_T\times I_S(\lambda,x,y) \quad [\text{Eq. 7}]$$

For the case of a point source, we can reformulate $I_0$ in terms of the peak output intensity $I_S$ and radiance distribution $\delta_S$ of the light source as per Equation 8.

$$I_0(\lambda, x, y) = C_T \times \frac{\hat{I}_S \times \delta_S(\lambda, \varphi)}{v(x, y)^2} \quad [\text{Eq. 8}]$$

This equation assumes radiance with cylindrical symmetry about the normal of the point source, where the absorption and scattering of light outside the medium are considered negligible and the loss of intensity with distance travelled follows the inverse square law. This equation enables the projection of radiance from the point source onto the flat outer surface of a medium, where $z_s$ is the normal distance between the point source and said surface. Here, the angle of radiance from the normal of the light source is $\varphi=z_s/v(x,y)$, $0 \leq \rho \leq \pi/2$, and the path length of light incident on the surface of the medium at position (x, y), is $v(x,y)=\sqrt{x^2+y^2+z_s^2}$.

Assuming cylindrical symmetry and optical homogeneity of the medium, the optical density $\rho$ for a source light at wavelength λ can be formulated as a function of the source-detector separation l' as per Equation 9.

$$\rho(\lambda,l')=\Sigma_{i=1}^{N}(\mu_{ai}(\lambda)\times L(\mu_{si}(\lambda),l')) \quad [\text{Eq. 9}]$$

In this equation the source-detector separation is defined in terms of a light source at point $(x_s,y_s)$ and an arbitrary detector at point (x,y) on the surface of the medium, i.e., $$l'(x,y)=\sqrt{(x-x_s)^2+(y-y_s)^2}.$$

We can now reformulate Equation 1 by integrating the light entering the medium $I_0(\lambda,x,y)$ across the entire surface of the medium as per Equation 10.

$$dP(\lambda,x,y)=\iint I_0(\lambda,x',y')\times e^{-\rho(\lambda,l')}dx'dy' \quad [\text{Eq. 10}]$$

This equation describes the infinitesimal transmitted optical power dP at point (x,y). For a detector of a finite rectangular area on the surface of the medium defined by vectors x and y, spanning from $x_-$ to $x_+$ and from $y_-$ to $y_+$, we can derive the optical power received by the detector as per Equation 11.

$$P(\lambda,x,y)=\int_{x_-}^{x_+}\int_{y_-}^{y_+}dP(\lambda,x_d,y_d)dx_ddy_d \quad [\text{Eq. 11}]$$

We now consider the case of a dynamic medium (e.g. a tissue through which blood is pulsed) with a time-variant transmission of light, i.e., I(λ,t), where Equation 1 can be reformulated as per Equation 12.

$$I(\lambda,t)=I_0(\lambda)\times e^{-\rho(\lambda,t)} \quad [\text{Eq. 12}]$$

In this equation, the dynamic optical density for the medium models the dynamic properties of the medium. In a real system, these dynamic properties arise from the physiology of the body tissue site and manifest as changes in its geometry and its absorption and scattering properties. For the more complex case of an N-layered medium comprising a 2-dimensional (flat) outer surface, we can model the dynamic nature of the medium using pulsatility coefficients $\mu_{pi}(\lambda)$, where the layer number i ranges from 1 to N, and a normalised physiological pulse function $\psi(t)$, as per Equation 13.

$$\rho(\lambda,l',t)=\Sigma_{i=1}^{N}(\mu_{ai}(\lambda)\times L(\mu_{si}(\lambda),l')\times(1+\mu_{pi}(\lambda)\times\psi(t))) \quad [\text{Eq. 13}]$$

It follows that the optical density can be separated into static $\bar{\rho}(\lambda,l')$ and dynamic $\tilde{\rho}(\lambda,l',t)$ components as per Equations 14 to 16.

$$\rho(\lambda,l',t)=\bar{\rho}(\lambda,l')+\tilde{\rho}(\lambda,l',t) \quad [\text{Eq. 14}]$$

$$\bar{\rho}(\lambda,l')=\Sigma_{i=1}^{N}(\mu_{ai}(\lambda)\times L(\mu_{si}(\lambda), l')) \quad [\text{Eq. 15}]$$

$$\tilde{\rho}(\lambda,l',t)=\Sigma_{i=1}^{N}(\mu_{ai}(\lambda)\times L(\mu_{si}(\lambda),l')\times\mu_{pi}(\lambda)\times\psi(t)) \quad [\text{Eq. 16}]$$

Using the sum rule of integration on Equations 10 and 11, we can similarly define the static $\bar{P}(\lambda,x,y)$ and dynamic $\tilde{P}(\lambda,x,y,t)$ components of transmitted optical power for a rectangular detector defined by vectors x and y as per Equations 17 to 21.

$$P(\lambda, x, y, t) = \bar{P}(\lambda, x, y) + \tilde{P}(\lambda, x, y, t) \quad [\text{Eq. 17}]$$

$$\bar{P}(\lambda, x, y) = \int_{x_-}^{x_+} \int_{y_-}^{y_+} d\bar{P}(\lambda, x_d, y_d)dx_ddy_d \quad [\text{Eq. 18}]$$

$$\bar{P}(\lambda, x, y) = \quad [\text{Eq. 19}]$$

$$\int_{x_-}^{x_+}\int_{y_-}^{y_+}\left(\iint I_0(\lambda, x', y')\times e^{-\bar{\rho}(\lambda,l'(x',y'))}dx'dy'\right)dx_ddy_d$$

$$\tilde{P}(\lambda, x, y, t) = \int_{x-}^{x+} \int_{y-}^{y+} d\tilde{P}(\lambda, x', y', t) dx_d dy_d \quad [\text{Eq. 20}]$$

$$\tilde{P}(\lambda, x, y, t) =$$
$$\int_{x-}^{x+} \int_{y-}^{y+} \left( \int \int I_0(\lambda, x', y') \times e^{-\tilde{p}(\lambda, l'(x', y'), t)} dx' dy' \right) dx_d dy_d \quad [\text{Eq. 21}]$$

We now consider a practical use of the opto-physiological model 14 in the design of an opto-physiological sensor such as sensor 12. To this end, we can define the quality Q of a detected signal in terms of its normalised peak dynamic power as per Equation 22.

$$Q(\lambda) \propto |\min_t(\tilde{P}(\lambda, x, y, t))| / \overline{P}(\lambda, x, y) \quad [\text{Eq. 22}]$$

In this equation, the peak dynamic power is defined using the minimum value of the dynamic power as the strongest power transient originates at systolic heart pressure, which manifests as a trough in the optical signal acquired from the sensor. It follows that we can define an optimum source-detector separation l'(λ) for a light source at wavelength λ as per Equation 23.

$$l'(\lambda) = \max_{(x, y)}(|\min_t(\tilde{P}(\lambda, x-x, y-y, t))| / \overline{P}(\lambda, x-x, y-y)) \quad [\text{Eq. 23}]$$

Assuming cylindrical symmetry and optical homogeneity of the medium as before, the optimum source-detector separation l'(λ) can be expressed as a circle centred on the position of the light source $(x_s, y_s)$, or conversely centred on the position of the detector $(x_d, y_d)$, as per Equation 24.

$$l'(\lambda) = \sqrt{(x-x_s)^2 + (y-y_s)^2} = \sqrt{(x-x_d)^2 + (y-y_d)^2} \quad [\text{Eq. 24}]$$

Finally, we consider the practical use of the opto-physiological model 14 in the determination of physiological parameters using signals acquired from an opto-physiological sensor such as the sensor 12. The determination of said parameters typically relies on knowledge of the temporal locations of systolic peaks apparent in the detected signals. Equation 25 defines the time location of a single systolic peak $t_n$ as the local minimum of a single period in a physiological pulse wave, said period occurring between times $t_{an}$ and $t_{bn}$.

$$t_n = |\min_t(\tilde{P}(\lambda_n, x, y, t))|, \; t_{an} < t < t_{bn} \quad [\text{Eq. 25}]$$

We consider the oxygen saturation in arterial blood S, which can be defined as a function of the ratio R of normalised dynamic intensities $R_1$ and $R_2$ originating from illumination at two wavelengths $\lambda_1$ and $\lambda_2$ as per Equations 26 to 28.

$$R_n = |\min_t(\tilde{P}(\lambda_n, x, y, t))| / \overline{P}(\lambda_n, x, y) \quad [\text{Eq. 26}]$$

$$R = R_1 / R_2 \quad [\text{Eq. 27}]$$

$$S = (C_1 - C_2 \times R) / (C_3 - C_4 \times R) \quad [\text{Eq. 28}]$$

The calibration constants $C_1$ to $C_4$ in Equation 28 are dependent on the optical characteristics for the light sources emitting at the two distinct wavelengths $\lambda_1$ and $\lambda_2$ and can be determined through a calibration procedure of the opto-physiological sensor.

We can also consider the pulse-to-pulse intervals (PPI), which can be defined as the time intervals $\Delta t_1, \Delta t_2, \ldots m \; \Delta t_{N-1}$ between adjacent systolic peaks occurring at times $t_1, t_2, t_N$ as per Equation 29.

$$\Delta t_n = t_{n+1} - t_n \quad [\text{Eq. 29}]$$

The time intervals $\Delta t_n$ can subsequently be used to calculate statistical measures relevant to the physiological status of the subject.

A suitable opto-physiological model 14 for use in embodiments of the present invention may thus comprise any or all of the following:

i) One or more of the equations detailed herein, their substitutions, or discrete derivations (i.e., numerically solvable formulations) thereof;
 ii) Numerical or mathematical descriptions of one or more light sources including their emission wavelengths and spatial distributions;
 iii) Numerical or mathematical descriptions of the body tissue site including the thicknesses and the static and dynamic optical properties of a set of layers of tissue (e.g., epidermis, superficial dermis, superficial dermal plexus, deep dermis, deep dermal plexus, sub-cutaneous fat);
 iv) Numerical or mathematical descriptions of effective path lengths L as a function of source-detector separation $I_{s\text{-}d}$ and scattering coefficients $\mu_s$, derived, for example, using finite element solutions of the Radiative Transport Equation or its P1 (diffusion) approximation, applied to the 3-dimensional geometric model of the body tissue site of interest.

Thus, combining the elements of model 14 and using a set of opto-physiological properties that are specific for the body tissue to be monitored, we can derive the optimum location for the light sources 28 and photodetector 30 of the OP sensor 12.

Figure 2:
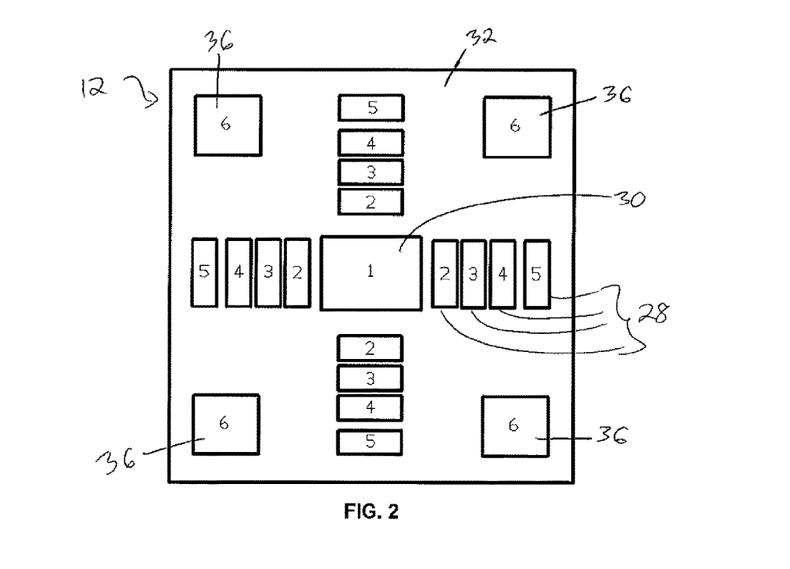
FIG. 2 shows a schematic top view of an OP sensor in accordance with an embodiment of the present invention.

As best illustrated in FIG. 2, in the OP sensor 12 designed by the model 14, the photodetector 30 is substantially rectangular and is provided in the centre of a square patch 32 such that it can capture radiation originating from each of the plurality of light sources 28, after light from each light source 28 has travelled through body tissue being monitored. In this embodiment, the light sources 28 are distributed around the photodetector 30, extending in four rows which are aligned with each side of the photodetector 30. It will be understood that each row of light sources 28 will be configured to generate light at one of four different wavelengths. Each row is therefore positioned on the circumference of a circle 34 (see FIG. 1) that is centred on the photodetector 30, such that the radius of each circle 34 is based on the optimum separation 26 which has been determined for light at the wavelength of the respective light sources 28 in that row.

FIG. 2 also shows the positions of four additional (optional) sensing elements 36 in each corner of the patch 32. The sensing elements 36 may be constituted by, for example, temperature sensors or motion sensors and such sensing elements may be based on a variety of techniques, including optical, opto-acoustic, acoustic or electro-mechanical.

Figure 3A:
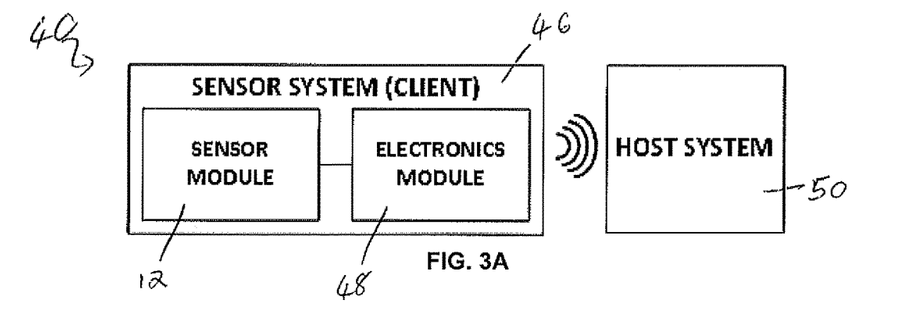
FIG. 3A shows a schematic view of a first OP system in accordance with an embodiment of the present invention.
Figure 3B:
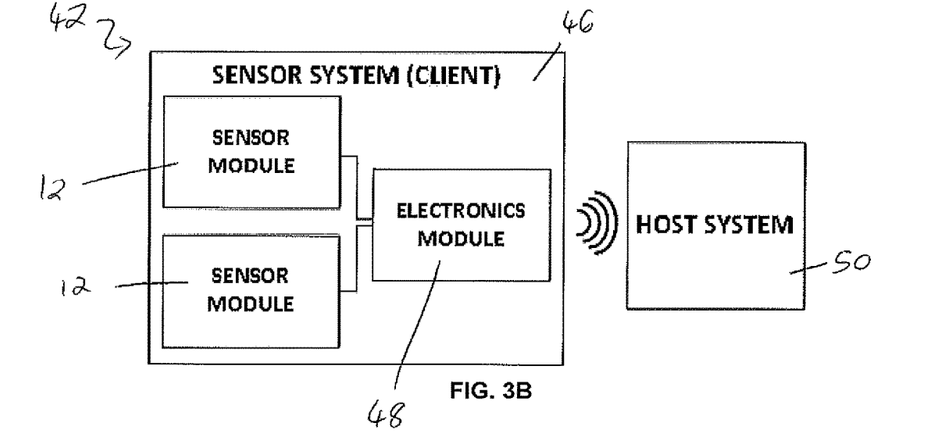
FIG. 3B shows a schematic view of a second OP system in accordance with an embodiment of the present invention.
Figure 3C:
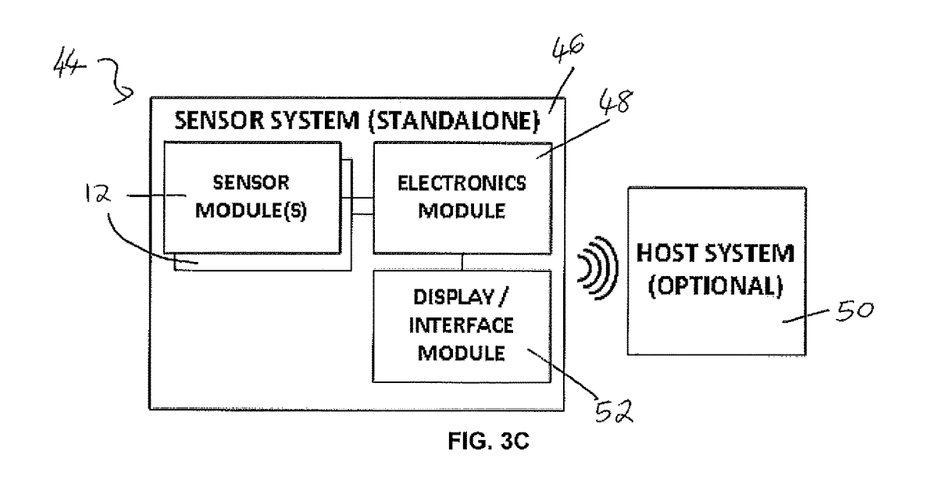
FIG. 3C shows a schematic view of a third OP system in accordance with an embodiment of the present invention.

FIGS. 3A, 3B and 3C show schematic views, respectively, of a first 40, second 42 and third 44 OP system in accordance with embodiments of the present invention.

The first OP system 40 comprises a client device 46 which comprises the OP sensor 12 described above plus an electronic controller 48. As described in more detail below, the controller 48 is operable to activate or deactivate the plurality of light sources 28 of the sensor 12. In addition, the controller 48 comprises an analogue-to-digital converter 58 configured to receive a sequence of measured intensities from the photodetector 30. In cases where the measured intensities from the photodetector 30 are to be interpreted as multiple (i.e., multiplexed) signals, the controller 48 is configured to separate (i.e., de-multiplex) these signals. The controller 48 also comprises a signal processing analyser 64 configured to separate and measure the static and dynamic components in one or more signals acquired by the photodetector 30 and to subsequently use these measurements to determine one or more physiological parameters therefrom (e.g. blood oxygen saturation, heart rate, pulse rate velocity, respiration rate, blood pressure, body temperature or an indication of a user's state or mood).

The signal processing analyser 64 can be configured to separate the static and dynamic components of one or more detected signals through the use of one or more digital filters, and to subsequently measure the amplitude of these static and dynamic components. The frequency bands of said filters can be set according to which physiological parameters are to be determined, the level of accuracy that is required by the application, and the level of noise that is encountered in each signal. Once separated, the amplitude of the each static component is readily available. The amplitude of each dynamic component can be determined by detecting the amplitude of peaks, or alternatively, by detecting the amplitude of peaks and troughs and subsequently taking the absolute value of the difference between adjacent peaks and troughs. Alternatively, the signal processing analyser 64 can be configured to convert each signal to its corresponding frequency spectrum using a Fast Fourier Transform. The amplitude of static and dynamic components can subsequently be measured by determining the amplitudes of peaks in each frequency spectrum.

The signal processing analyser 64 of the present embodiment is configured to use the opto-physiological model 14 described above, to derive the physiological parameter of interest from the measurements of said static and dynamic components of the measured signals.

The controller 48 further comprises the means to adjust certain parameters pertaining to the control of the sensor elements; for example, which light sources 28 are to be modulated, the rate at which the light sources 28 are modulated, the rate at which samples are acquired from the photodetector 30, and the filter parameters used by the signal processing analyser 64. The OP system 40 can be configured to make said adjustments according to quality metrics acquired during the course of operation of the OP system and/or according to a user-defined mode of operation for said system. Further, said adjustments can be made without interrupting the course of operation of the OP system 40.

The controller 48 further comprises a wireless communications function 66, 68 configured to send data relating to the determined physiological parameters to a host system 50. The host system 50 can be provided by a local computer or a networked server. The host system 50 is provided with a user interface to allow a user to select a physiological parameter to be monitored, a display to communicate the determined physiological parameter to a user and a data management system for storing the determined physiological parameters for future use.

The second OP system 42 is substantially similar to the first OP system 40 but comprises two OP sensors 12 linked to the single electronic controller 48. Each OP sensor 12 may be substantially similar such that the electronic controller 48 can combine the detected signals to give a more accurate determination of the physiological parameter being measured. Alternatively, each OP sensor 12 may be configured for used on a different body tissue type (e.g. finger or neck) and the electronic controller 48 can be configured to select the OP sensor 12 to be used for a particular application.

The third OP system 44 is substantially similar to the second OP system 42 but wherein the client device 46 is configured as a standalone system, with communication to the host system 50 being provided as an optional feature. Thus, the client device 46 further comprises a user interface 52 configured to allow a user to select a physiological parameter to be monitored and including a display to communicate the determined physiological parameter to a user. The client device 46 may optionally also include a data management system for storing the determined physiological parameters for future use.

Figure 4A:
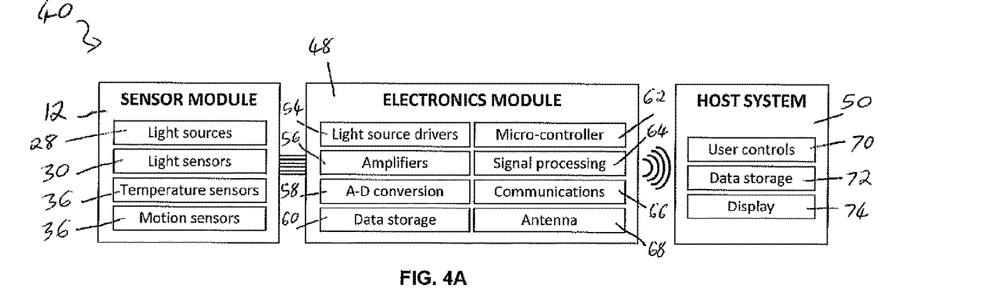
FIG. 4A shows a more detailed schematic view of the OP system of FIG. 3A.
Figure 4B:
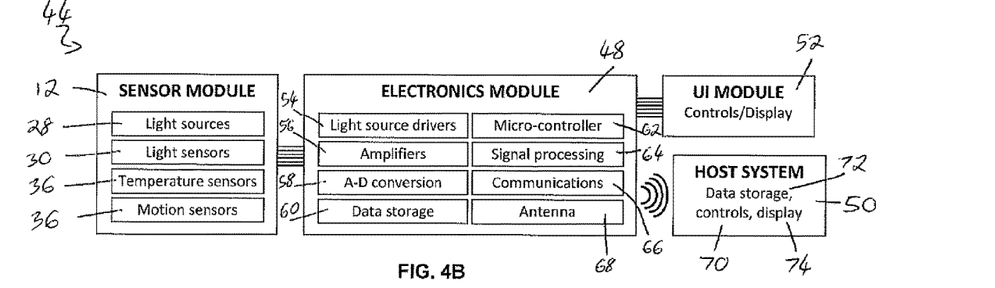
FIG. 4B shows a more detailed schematic view of the OP system of FIG. 3C.

FIGS. 4A and 4B show more detailed schematic views of the first 40 and third 44 OP systems described above. In each case, the OP sensor 12 comprises light sources 28, one or more light sensors (e.g. photodetector 30), temperature sensors and motion sensors 36 for example, as arranged in FIG. 2. In addition, the electronic controller 48 comprises light source drivers 54, amplifiers 56, an analogue to digital converter 58, data storage 60, a micro-controller 62, a signal processing analyser 64 (described above), a communications system 66 and an antenna 68. As explained above, the host system 50 (which is optional in FIG. 4B) comprises a user interface in the form of user controls 70, data storage 72 and a display 74. The standalone OP system 44 of FIG. 4B also comprises the user interface 52 described above. It will be understood, by persons skilled in the art, how to configure these components to produce a working OP system as described.

In particular embodiments, the OP sensor 12 may be configured (e.g. through multiplexing) such that independent signals are obtainable from the exclusive contribution of each individual light source 28 (or each row of light sources 28) to an output from the photodetector 30. Furthermore, the controller 48 may be configured to selectively activate and/or deactivate light sources 28 based on a signal quality metric. For example, the controller 48 may be configured to: obtain independent signals from the contribution of each individual light source 28 to an output from the photodetector 30; perform one or more measurements of signal quality on each independent signal; modify the illumination intensities of each individual light source 28 and repeating the measurements of signal quality; further modify the intensities of individual light sources 28 whose independent signals have undergone a rise in signal quality and repeat the measurements of signal quality; reverse the modification of intensities of individual light sources 28 whose independent signals have undergone a drop in signal quality and repeat the measurements of signal quality; fix the intensities of individual light sources 28 whose corresponding signals have reached a peak in signal quality; and selectively deactivate light sources 28 whose independent signals are below a threshold value. Thus, the controller 48 may be configured to optimise the signal strength from each individual light source 28. This may be performed as an initialising step in order to ensure that each light source is operating in a steady-state condition prior to further processing such as for the assessment of signal quality described below in relation to FIG. 6.

As mentioned previously, the use of multiple light sources 28 can ensure that there is more than one available pathway for light to travel through the body tissue to be monitored to the photodetector 30. It is therefore possible for the signal quality metric to be applied so as to separate or eliminate noisy or poor quality signals so that the output from the photodetector 30 is more accurate and reliable. Using such techniques, embodiments of the invention can be employed to automatically adjust the sensor characteristics for the body tissue being monitored (e.g. by changing the light sources or wavelengths activated and the intensity of the same) during use so as to optimise the quality of the signals detected. Accordingly, not only is the present sensor designed through application of an opto-physiological model of the tissue type (or types) to be monitored but it is also able to dynamically adjust its settings during use, for example, to take into account the age of the user or an accumulation of sweat or creams applied to the skin.

Figure 5:
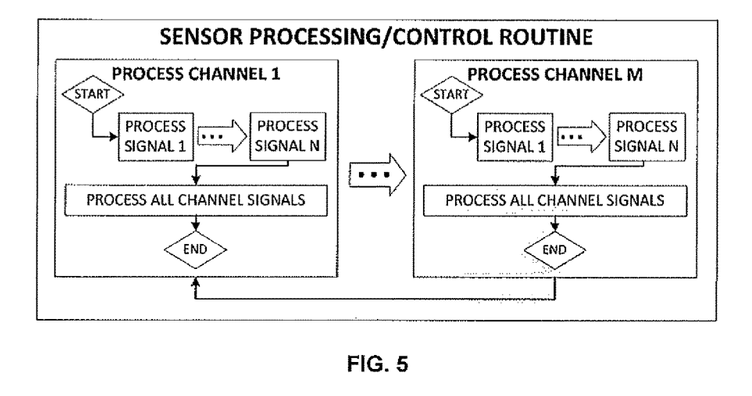
FIG. 5 illustrates a general sensor processing/control routine that may be employed in embodiments of the present invention.

FIG. 5 illustrates a general sensor processing/control routine that may be employed in embodiments of the present invention. In this case, multiple light source channels (designated 1 to M) are provided with each channel comprising a number of light sources (designated 1 to N) which are configured to generate light at the same wavelength. The light sources making up each channel (and having the same wavelength) are disposed at the same distance from a photodetector and different channels are disposed at different distances to the photodetector, based on the signal quality calculations as per Equation 22 of the OPM.

As illustrated, the first channel is processed (e.g. by the electronics module 48) by sequentially processing signals obtained from each individual light source until the signals from each source in the channel have been assessed as described below in relation to FIG. 6. This process is then repeated for each light source making up the next and each subsequent channel.

Figure 6:
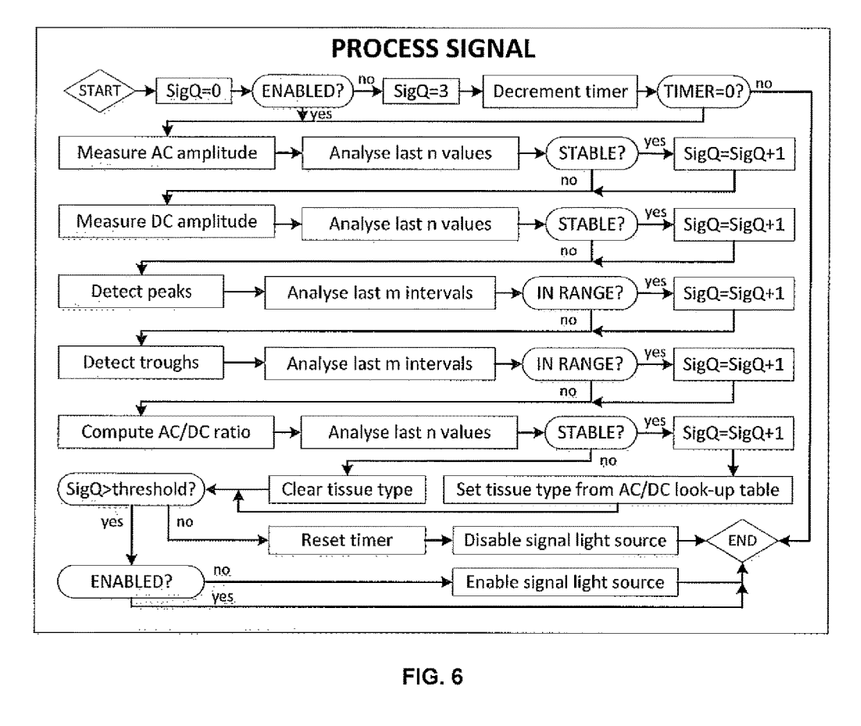
FIG. 6 illustrates a signal processing routine that may be employed for signals originating from individual light sources, and for control of said light sources in embodiments of the present invention.

The processing of a signal from each individual light source is shown in FIG. 6 and comprises setting a signal quality value (SigQ) initially to 0 (e.g. on a scale of, say 0-6 where 0 represents a low quality signal and 6 represents a high quality signal). The system then check whether the light source has been enabled and, if so, measures an AC amplitude of the signal captured by the photodetector. If the signal is not enabled, the light source is switched on and a signal quality value is set to 3 (so that fewer readings are required) and the system will check to determine whether to re-enable the light source. In which case, a timer may be employed to introduce a delay of e.g. 0.5 s or 1 s before the AC amplitude of the signal captured by the photodetector is measured. This helps to ensure that a stable measurement is used after the light source is initially switched on.

When measuring the AC amplitude, the last n measured values of AC amplitude taken from the light intensity of the photodetector are recalled, and a determination is made as to whether the AC amplitude is stable. If the AC amplitude is stable the signal quality value is incremented by 1 before the DC amplitude of the signal captured by the photodetector is measured. If the AC amplitude is not stable (e.g. has a variability that goes beyond a threshold value), the signal quality value is not incremented before the DC amplitude is measured.

As above, when measuring the DC amplitude, the last n measured values of DC amplitude taken from the light intensity of the photodetector are recalled, and a determination is made as to whether the DC amplitude is stable. If the DC amplitude is stable the signal quality value is incremented by 1 before peaks in the signal captured by the photodetector are determined. If the DC amplitude is not stable (e.g. has a variability that goes beyond a threshold value), the signal quality value is not incremented before the peaks are determined.

The time intervals between the last m successive peaks are then recalled and measured and a determination made as to whether the intervals are within a predefined range which is dependent on the physiological parameters being measured. If the intervals are within range the signal quality value is incremented by 1 before troughs in the signal captured by the photodetector are determined. If the intervals are not within range, the signal quality value is not incremented before the troughs are determined.

As above, the time intervals between the last m successive troughs are then recalled and measured and a determination made as to whether the intervals are within a predefined range which is dependent on the physiological parameters being measured. If the intervals are within range the signal quality value is incremented by 1 before an AC/DC ratio is calculated. If the intervals are not within range, the signal quality value is not incremented before the AC/DC ratio is calculated.

If the AC/DC ratio is stable over the last n values, the signal quality value is incremented by 1 before the tissue type is determined from an AC/DC look-up table. If the AC/DC ratio is not stable, the tissue type is cleared. In both cases, the signal quality value is then compared against a threshold value (of, say, 4 or 5) and if the signal quality value is greater than the threshold the light source is enabled. However, if the signal quality value is not greater than the threshold, the timer is reset and the light source is disabled.

It will be understood that the AC/DC ratio can effectively give a ratio of the static and dynamic components of the effective optical path length through the body tissue. The look-up table is preferably created using an opto-physiological model such as described above. It may therefore take into account the wavelengths and path lengths employed so as to accurately relate the AC/DC ratio to a particular tissue type.

In embodiments of the invention, the process of FIG. 6 may therefore be employed to assess the signal quality of each individual light source for each channel and to determine a tissue type based on the static and dynamic portions of the signals originating from each of said light sources.

Figure 7:
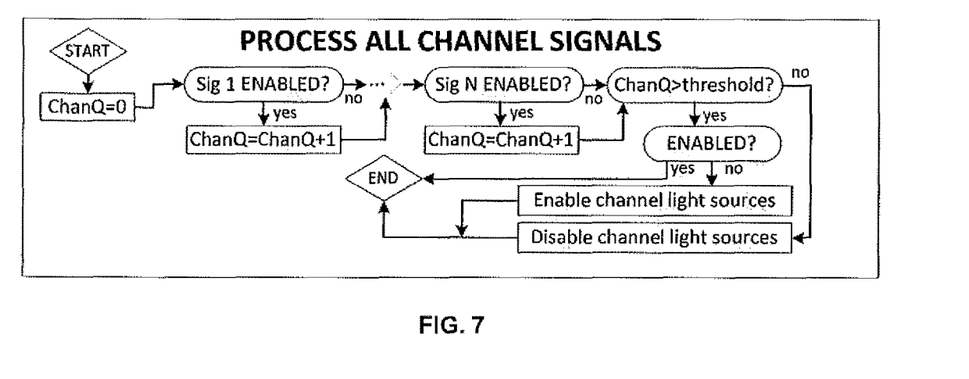
FIG. 7 illustrates a process for selecting a light channel comprising one or more light sources to use in embodiments of the present invention.

A process for selecting which light channel (as opposed to which individual light source per channel) to use in embodiments of the present invention is illustrated in FIG. 7. In this case, a channel quality value ChanQ is initially set to 0 and the signal from each individual light source in each channel is checked in turn to determine which are enabled (e.g. based on the process of FIG. 6). For each light source that is enabled the channel quality value is incremented by one and if the total channel quality value for each channel exceeds a predetermined threshold, said channel will be enabled. However, if the total channel quality value does not exceed the threshold, that channel will be disabled. In this way, the channels having the most enabled light sources will be preferentially selected for use in further measurements (e.g. to determine a desired physiological parameter). Further, the knowledge of channel quality may be used to determine the reliability of certain physiological parameters.

It will be appreciated by persons skilled in the art that various modifications may be made to the above embodiments without departing from the scope of the present invention. For example, features described in relation to one embodiment may be mixed and matched with features described in relation to one or more other embodiments.

What is claimed is:

1. An opto-physiological sensor comprising:
a plurality of light sources; and
at least one photodetector mounted to the sensor and configured to capture radiation originating from one or more of said light sources, after light from said light source has travelled through a body tissue type to be monitored,
wherein the plurality of light sources are mounted to the sensor in fixed positions relative to the photodetector, the fixed positions being based on a model of the opto-physiological properties of the body tissue type to be monitored, wherein the separation of each light source from the photodetector is based on modelled optical path lengths for light travelling from each light source, through the body tissue type to be monitored, to the photodetector; and wherein a plurality of light sources of a first wavelength are positioned in a first array on the circumference of a first circle, the first circle being centered on the photodetector and having a radius based on the first wavelength, wherein a plurality of light sources of a second wavelength are positioned in a second array on the circumference of a second circle, the second circle being centered on the photodetector and having a radius based on the second wavelength, wherein each of the first and second arrays comprises at least four light sources.

2. The opto-physiological sensor according to claim 1 wherein multiple light sources are configured to generate light at the same wavelength or waveband and the sensor is operable to select one or more of said multiple light sources for use in an opto-physiological measurement based on the captured radiation quality.

3. The opto-physiological sensor according to claim 1, further comprising a controller operable to activate and deactivate the plurality of light sources based on a measured signal from the photodetector.

4. An opto-physiological system comprising:
an opto-physiological sensor according to claim 1; and
an analyser configured to analyse a signal measured by the photodetector to determine at least one physiological parameter therefrom.

* * * * *